US011858883B2

(12) United States Patent
Chen et al.

(10) Patent No.: US 11,858,883 B2
(45) Date of Patent: Jan. 2, 2024

(54) METHOD FOR RECYCLING TAURINE MOTHER LIQUOR

(71) Applicant: QIANJIANG Yongan Pharmaceutical CO., LTD., Hubei (CN)

(72) Inventors: Yong Chen, Qianjiang (CN); Xiquan Fang, Qianjiang (CN); Shaobo Li, Qianjiang (CN); Feng Liu, Qianjiang (CN)

(73) Assignee: QIANJIANG YONGAN PHAMACEUTICAL CO., LTD., Qianjiang (CN)

( * ) Notice: Subject to any disclaimer, the term of this patent is extended or adjusted under 35 U.S.C. 154(b) by 0 days.

(21) Appl. No.: 17/693,451

(22) Filed: Mar. 14, 2022

(65) Prior Publication Data
US 2023/0212111 A1  Jul. 6, 2023

(30) Foreign Application Priority Data

Dec. 24, 2021  (CN) .......................... 202111602226.5

(51) Int. Cl.
*C07C 303/32* (2006.01)
*C07C 303/44* (2006.01)
*C07C 303/22* (2006.01)

(52) U.S. Cl.
CPC .......... *C07C 303/32* (2013.01); *C07C 303/44* (2013.01); *C07C 303/22* (2013.01)

(58) Field of Classification Search
None
See application file for complete search history.

(56) References Cited

U.S. PATENT DOCUMENTS 9,745,258 B1 * 8/2017 Hu ......................... C07C 303/44
2014/0121405 A1 * 5/2014 Chen ..................... C07C 303/18
562/104

(Continued)

FOREIGN PATENT DOCUMENTS

CN 105732440 * 7/2006 ........... C07C 303/02
CN 101486669 A 7/2009

(Continued)

*Primary Examiner* — Amy C Bonaparte
(74) *Attorney, Agent, or Firm* — Kilpatrick Townsend & Stockton LLP

(57) ABSTRACT

The present disclosure relates to a method for recycling a taurine mother liquor, which includes: adding a base to the taurine mother liquor, heating to a first temperature, carrying out a hydrolysis reaction, removing ammonia produced, and evaporating and concentrating the ammonia-removed solution to obtain an alkali metal hydroxyethyl sulfonate solution. When applying the method provided by the present disclosure for the recycling of the taurine mother liquor, the taurine mother liquor can be further converted into the alkali metal hydroxyethyl sulfonate solution, impurities are removed from the obtained alkali metal hydroxyethyl sulfonate solution, the impurity-removed alkali metal hydroxyethyl sulfonate solution is concentrated and crystallized, and the alkali metal hydroxyethyl sulfonate is separated out. The method provided by the present disclosure is an efficient and simple method for recycling the taurine mother liquor, which is very easy to implement industrially and can effectively recycle the taurine mother liquor.

19 Claims, 4 Drawing Sheets

(56) References Cited

U.S. PATENT DOCUMENTS

| | | | |
|---|---|---|---|
| 2021/0061758 A1* | 3/2021 | Chen ................... | B01D 15/363 |
| 2021/0114978 A1* | 4/2021 | Chen ................... | C07C 303/22 |

FOREIGN PATENT DOCUMENTS

| | | | |
|---|---|---|---|
| CN | 101508657 | A | 8/2009 |
| CN | 101508658 | A | 8/2009 |
| CN | 101508659 | A | 8/2009 |
| CN | 110483342 | A | 11/2019 |
| CN | 111233717 | A | 6/2020 |
| CN | 111620796 | A | 9/2020 |
| CN | 112570001 | A | 3/2021 |
| CN | 112979508 | A | 6/2021 |
| EP | 3808734 | A1 | 4/2021 |
| IN | 110590613 | A | 12/2019 |

* cited by examiner

METHOD FOR RECYCLING TAURINE MOTHER LIQUOR

CROSS-REFERENCE TO RELATED APPLICATION

This application claims the benefit of and the priority to Chinese Patent Application No. 202111602226.5, filed Dec. 14, 2021, entitled "Method For Recycling Taurine Mother Liquor," the disclosure of which is incorporated by reference herein in its entirety for all purposes.

FIELD

The present disclosure relates to a taurine production technology, in particular to a method for recycling a taurine mother liquor.

BACKGROUND

Taurine, having a chemical name of 2-aminoethanesulfonic acid, is the most abundant sulfur-containing free amino acid in cells of the body. The chemical synthesis route of taurine mainly includes an ethylene oxide method and an ethanolamine method. Wherein, the ethylene oxide method includes three steps as follows:

With ethylene oxide as a starting material, ethylene oxide and sodium bisulfite are subjected to an addition reaction to obtain sodium hydroxyethyl sulfonate. Sodium hydroxyethyl sulfonate is subjected to ammonolysis to obtain sodium taurate. Then, sodium taurate is subjected to acidification, such as, by hydrochloric acid, sulfuric acid or ion exchange resin, electrodialysis, etc. to obtain taurine, and then taurine is separated and purified to obtain a product. The main reactions are as follows:

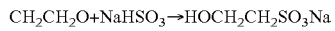

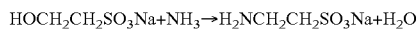

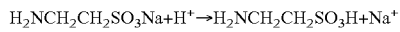

wherein a side reaction during the addition is as follows:

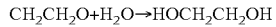

It is inevitable to produce by-products during the whole reaction process, including ethylene glycol and ethylene glycol polymers, hydroxyethyl sulfonic acid derivatives and taurine derivatives, etc. The ammonolysis reaction is reversible, and thus approximately more than 20% of sodium hydroxyethyl sulfonate will enter the next process along with the production system. After neutralization of the finished ammonolysis reaction solution, the separated mother liquor is concentrated, separated and extracted for 1-3 times to obtain a final mother liquor. The final mother liquor includes impurities mainly including taurine, sodium hydroxyethyl sulfonate, sodium sulfate, ethylene glycol and polyethylene glycol, etc., which are highly polluting emissions. The existing production methods are subjected to a problem of increased by-product accumulation when the mother liquor used is recycled. When the by-products reach a threshold value, the problem can only be solved by discharging part of the mother liquor, which causes waste and pollution.

Chinese patents CN101508657A, CN101508658A, CN101508659A and CN101486669A describe a method for using sulfuric acid to neutralize sodium taurate, thereby obtaining taurine and sodium sulfate. Crude taurine can be easily obtained by filtering a crystal suspension after cooling. However, a waste mother liquor still contains taurine, sulfate and other organic impurities.

Chinese patent CN112570001A describes an amino-functionalized catalyst and a preparation method thereof and a method for removing impurities of ethylene glycol and its derivatives from a taurine mother liquor, in which the catalyst preparation process uses a large amount of organic substances, the preparation method and its operation are complicated, while new impurities are introduced.

Chinese patent CN111233717A describes a method for efficient separation of useful components from a taurine crystallization mother liquor, including with the taurine crystallization mother liquor as a raw material, firstly removing a sulfate by a barium chloride precipitation method, then converting effective components into taurine and hydroxyethyl sulfonic acid by acidification with hydrochloric acid, further esterifying the taurine and the hydroxyethyl sulfonic acid by using ethanol to generate an esterification product, transferring to an oil phase, separating the oil phase, then hydrolyzing to obtain taurine and hydroxyethyl sulfonic acid, and finally successively separating hydroxyethyl sulfonic acid and taurine by evaporation crystallization and cooling crystallization, and carrying out a neutralization reaction on hydroxyethyl sulfonic acid by using sodium hydroxide to obtain sodium hydroxyethyl sulfonate. In this method, heavy metal barium is introduced, and will have trace residues and affects the subsequent product quality, while new impurities such as ethanol are used in the production process.

Therefore, how to study effective recycling of the taurine mother liquor is a very important topic.

SUMMARY

The object of the present disclosure is to provide a method for recycling a taurine mother liquor for solving the problem of poor efficiency of recycling the taurine mother liquor in the prior art.

The present disclosure provides a method for producing an alkali metal hydroxyethyl sulfonate by using a taurine mother liquor, including: adding a base to the taurine mother liquor, heating to a first temperature, carrying out a hydrolysis reaction at the first temperature, removing ammonia produced, and evaporating and concentrating the ammonia-removed solution to obtain an alkali metal hydroxyethyl sulfonate solution.

According to one embodiment of the method for producing the alkali metal hydroxyethyl sulfonate by using the taurine mother liquor of the present disclosure, the method includes: removing impurities from the resulting alkali metal hydroxyethyl sulfonate solution, concentrating and crystallizing the impurity-removed alkali metal hydroxyethyl sulfonate solution, and separating the alkali metal hydroxyethyl sulfonate.

According to one embodiment of the method for producing the alkali metal hydroxyethyl sulfonate by using the taurine mother liquor of the present disclosure, the first temperature is 20-350° C. and the hydrolysis reaction is carried out for a period of greater than 1 min; preferably, the first temperature is 140-280° C. and the hydrolysis reaction is carried out for hours.

According to one embodiment of the method for producing the alkali metal hydroxyethyl sulfonate by using the taurine mother liquor of the present disclosure, the amount of the base is at least 20% of a molar amount of taurine in the mother liquor; preferably, a molar ratio of the taurine in the mother liquor to the base is 1:0.5 to 1.5.

According to one embodiment of the method for producing the alkali metal hydroxyethyl sulfonate by using the taurine mother liquor of the present disclosure, a method for removing the impurities is performed as follows: adding a decolorizing agent into the resulting alkali metal hydroxyethyl sulfonate solution for decolorization.

According to one embodiment of the method for producing the alkali metal hydroxyethyl sulfonate by using the taurine mother liquor of the present disclosure, the decolorizing agent is stirred for 0.5 to 5 h during the process of adding the decolorizing agent for the decolorization.

According to one embodiment of the method for producing the alkali metal hydroxyethyl sulfonate by using the taurine mother liquor of the present disclosure, the decolorizing agent is activated carbon or ion exchange resin, and activated carbon decolorization is carried out at 15-95° C., preferably 35° C-65° C.

According to one embodiment of the method for producing the alkali metal hydroxyethyl sulfonate by using the taurine mother liquor of the present disclosure, the concentrating and crystallizing is carried out at 20° C. to 80° C.

According to one embodiment of the method for producing the alkali metal hydroxyethyl sulfonate by using the taurine mother liquor of the present disclosure, the base added is an alkali metal hydroxide, an alkali metal carbonate compound or an alkali metal sulfite compound; preferably the alkali metal hydroxide; most preferably sodium hydroxide.

According to one embodiment of the method for producing the alkali metal hydroxyethyl sulfonate by using the taurine mother liquor of the present disclosure, ammonia is removed continuously during the conversion of the taurine mother liquor into the alkali metal hydroxyethyl sulfonate solution, and the removed ammonia is recycled.

According to one embodiment of the method for producing the alkali metal hydroxyethyl sulfonate by using the taurine mother liquor of the present disclosure, the separated alkali metal hydroxyethyl sulfonate is used to prepare sodium cocoyl hydroxyethyl sulfonate, sodium lauroyl hydroxyethyl sulfonate, sodium cocoyl methyl taurate, sodium lauroyl methyl taurate, 2-(N-morpholino)ethanesulfonic acid, sodium 2-(N-morpholino) ethanesulfonate, 2-(N-morpholino)ethanesulfonic acid monohydrate, 4-hydroxyethyl piperazinyl ethanesulfonic acid, sodium 4-hydroxyethyl piperazinyl ethanesulfonate, piperazine-N,N'-bis(2-ethanesulfonic acid), disodium piperazine-N,N'-bis(3-ethanesulfonate), hydroxyethyl sulfonic acid, sodium methyl taurate, methyl taurine and/or taurine.

According to one embodiment of the method for producing the alkali metal hydroxyethyl sulfonate by using the taurine mother liquor of the present disclosure, the taurine mother liquor is obtained by separating the obtained crude taurine during production of taurine.

According to one embodiment of the method for producing the alkali metal hydroxyethyl sulfonate by using the taurine mother liquor of the present disclosure, the separated alkali metal hydroxyethyl sulfonate is used in an ammonolysis reaction during production of taurine by an ethylene oxide method, so as to complete the recycling of the taurine mother liquor during the production of the taurine by the ethylene oxide method.

According to one embodiment of the method for producing the alkali metal hydroxyethyl sulfonate by using the taurine mother liquor of the present disclosure, the content of the alkali metal hydroxyethyl sulfonate in the alkali metal hydroxyethyl sulfonate solution is greater than 20%.

In summary, the present disclosure provides an efficient and simple method for producing the alkali metal hydroxyethyl sulfonate by using the taurine mother liquor. The method is very easy to implement industrially and can effectively recycle the taurine mother liquor.

DETAILED DESCRIPTION OF THE EMBODIMENTS

In order to illustrate the technical effects of the disclosure, the following examples are described. The following embodiments show the practice of the disclosure but are not intended to limit its scope. The raw materials used in the following embodiments are commercially available products unless otherwise specified, the methods used are conventional methods unless otherwise specified, and the material content refers to a mass-volume percentage unless otherwise specified. HPLC and LC-MS analysis shows the content of substances in the detection reaction.

In order to provide a generally simple and efficient method for recycling a taurine mother liquor, the inventors have conducted a lot of relevant researches and experiments.

After the inventor's experiments, it was found that under certain conditions, alkali metal taurate can be converted into alkali metal hydroxyethyl sulfonate. Under this inspiration, the inventors experimentally confirmed that the alkali metal hydroxyethyl sulfonate can be produced by repeatedly recycling the taurine mother liquor.

Therefore, this discovery allows the taurine mother liquor to be further recycled.

Based on the above experiments by the inventors, the present disclosure provides a method for producing an alkali metal hydroxyethyl sulfonate by using a taurine mother liquor, including:

after converting the taurine mother liquor into the alkali metal hydroxyethyl sulfonate, the content of the alkali metal hydroxyethyl sulfonate is increased, while since the solubility of the alkali metal hydroxyethyl sulfonate is very high, the separation of impurities is realized by adsorptive decolorization at a reduced temperature, and then the alkali metal hydroxyethyl sulfonate is separated by concentration and crystallization to obtain a high content of alkali metal hydroxyethyl sulfonate. The separated alkali metal hydroxyethyl sulfonate can be used as a raw material of taurine.

This embodiment realizes the recycling of the taurine mother liquor by converting the mother liquor into alkali metal hydroxyethyl sulfonate, thereby realizing recycling of taurine production.

Figure 1:
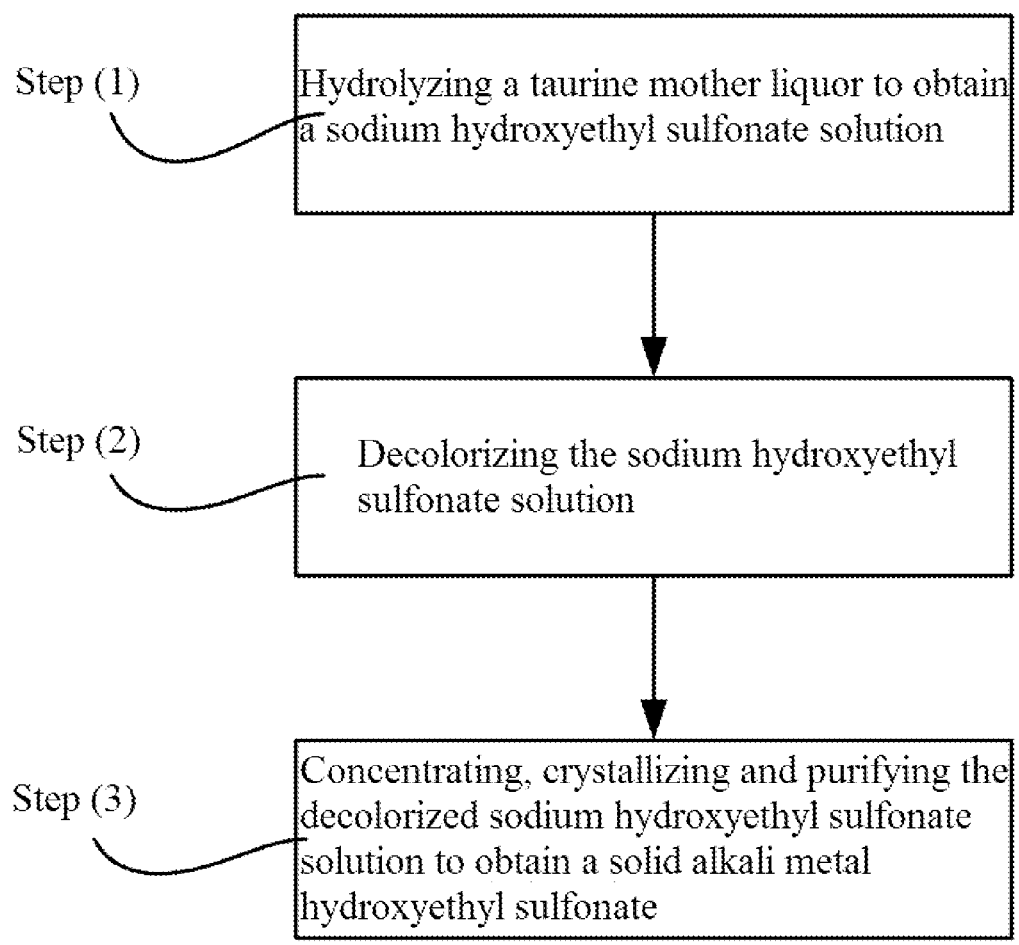
FIG. 1 shows a flow diagram of a method for producing an alkali metal hydroxyethyl sulfonate by using a taurine mother liquor.

The inventors also found that the mother liquor after extraction of taurine contains a certain amount of taurine. Sodium hydroxyethyl sulfonate and ammonia can be obtained by adding a base into the mother liquor and reacting at a certain temperature for a certain time. Therefore, it is also possible to provide a method of converting the taurine mother liquor into an alkali metal hydroxyethyl sulfonate solution, and use the alkali metal hydroxyethyl sulfonate solution, in combination with the aforementioned method for producing the alkali metal hydroxyethyl sulfonate by using the taurine mother liquor, for achieving the purpose of efficiently producing alkali metal hydroxyethyl sulfonate by recycling of the taurine mother liquor, as shown in FIG. 1, this embodiment further includes:

step (1): a hydrolysis step, including: an appropriate liquid base is added to the taurine mother liquor, and the obtained mixture is heated to a certain temperature, and subjected to a reaction for a period of time, and the resulting ammonia is continuously discharged and absorbed. Then the solution is appropriately evaporated and concentrated to obtain a sodium hydroxyethyl sulfonate solution having a content of greater than 20%; the above reaction can be carried out under any pressure, generally under atmospheric pressure.

After further experiments, the inventors found that the higher the temperature of the hydrolysis reaction within a certain range, the shorter the time required for the reaction and the higher the content of sodium hydroxyethyl sulfonate obtained, which indicates that the higher the temperature, the more conducive to the occurrence of hydrolysis. When the temperature exceeds a certain value, the content of sodium hydroxyethyl sulfonate will have a certain trend of decline, mainly because the temperature is too high, sodium hydroxyethyl sulfonate is unstable to be decomposed. While, if an appropriate alkali metal is added in the hydrolysis process, it will also be beneficial to hydrolysis.

Therefore, the hydrolysis is carried out for a period of at least greater than 1 minute, generally 0.5 h-5 h; the hydrolysis is carried out at 20-350° C., preferably 140-280° C.

The liquid base can be selected from an alkaline compound, such as alkali metal hydroxide, preferably sodium hydroxide. The amount of the added alkali metal can be preferably selected by a person skilled in the art. There is also a preferable solution, for example, if the alkali metal is added less, hydroxyethyl sulfonic acid will be present, which is unstable and easy to decompose, but the inventors found through the researches that it is preferred that a molar amount of the added alkali metal should be 0.2 times a molar amount of taurine or above. In addition to metal hydroxide, the compounds, such as an alkali metal carbonate compound and an alkali metal sulfite compound, can also be selected.

Therefore, the amount of the liquid base is at least 0.2 times the equivalent amount (a molar ratio) of taurine, wherein preferably, a molar ratio of taurine to the liquid base is 1:0.5 to 1.5.

The inventors also found that the continuous recycling of ammonia during the hydrolysis reaction facilitates the production of sodium hydroxyethyl sulfonate. According to the chemical equilibrium, the timely transfer of the resulting products is more favorable for the reaction to proceed toward the positive direction. Therefore, in addition to indirect ammonia discharge in the hydrolysis process, ammonia can also be recycled continuously in the reaction process.

Step (2): a step of decolorization and removing impurities, including: a decolorizing agent is added into the sodium hydroxyethyl sulfonate solution having the content of greater than 20% for decolorization, and stirred and then filtering is carried out.

The decolorizing agent can be ion exchange resin or activated carbon, etc.

Further, the decolorization reaction may be performed at a temperature of 10-100° C., wherein the step of decolorization and removing impurities is preferably performed at a temperature of 35° C.-65° C.

The stirring is carried out for a period of greater than 1 min, preferably 0.5-5 h.

Step (3): a concentrating and crystallizing step, including: the decolorized sodium hydroxyethyl sulfonate solution is concentrated, crystallized, purified, and separated to obtain a solid alkali metal hydroxyethyl sulfonate as well as a mother liquor.

Figure 2:
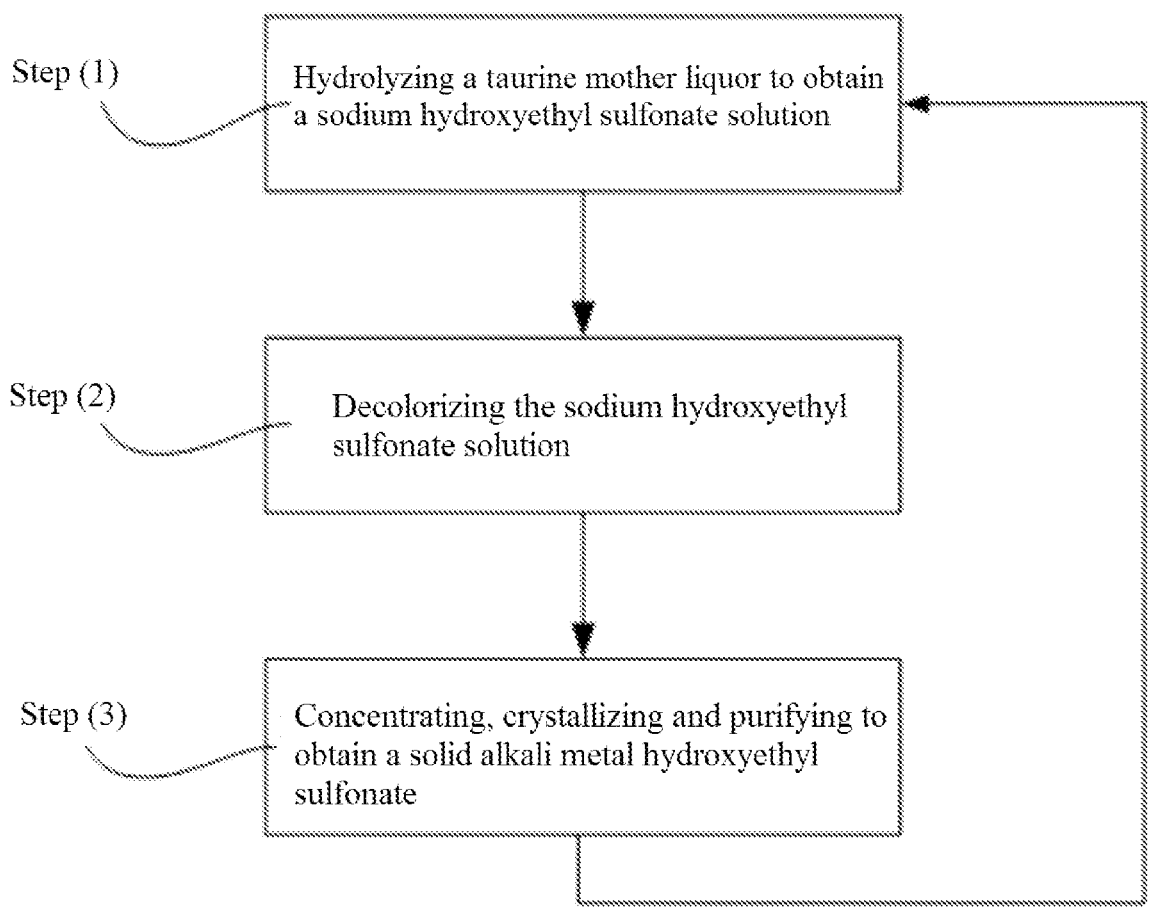
FIG. 2 shows a flow diagram of mother liquor recycling for hydrolysis in a method for producing an alkali metal hydroxyethyl sulfonate by using a taurine mother liquor.
Figure 3:
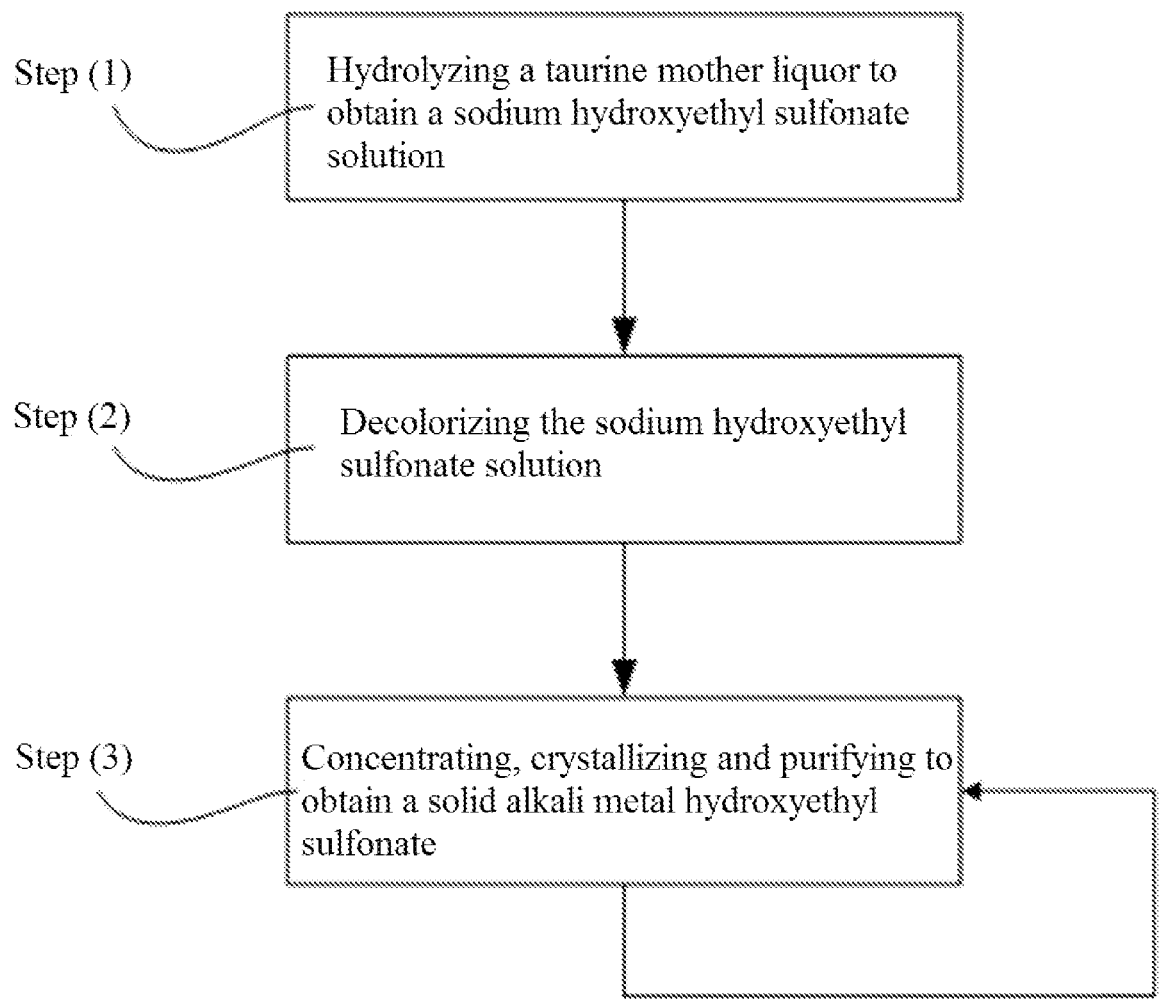
FIG. 3 shows a flow diagram of mother liquor recycling for crystallization and purification in a method for producing an alkali metal hydroxyethyl sulfonate by using a taurine mother liquor.

As shown in FIG. 2 and FIG. 3, the obtained solid hydroxyethyl sulfonate can be used as a raw material for cyclic production of taurine or as a raw material for other reactions. The mother liquor after concentrating and crystallizing can be crystallized and purified again for recycling, or can be directly returned to the step (1) as the taurine mother liquor for the hydrolysis reaction.

Wherein, the concentrating and crystallizing is carried out at 20° C.-150° C., preferably from 50° C.-80° C.

The concentrating and crystallizing can be carried out by intermittent or continuous concentration and crystallization such as single-effect, multi-effect, thermal vapor recompression (TVR), and mechanical vapor recompression (MVR).

Separation can be carried out by solid-liquid separation equipment, such as centrifugation, and filtration.

The inventors further found through research that the conversion of the taurine mother liquor into the alkali metal hydroxyethyl sulfonate solution can be cycled one or more times, that is, after the taurine mother liquor is hydrolyzed into a hydroxyethyl sulfonate solution by adding a base at a certain temperature and ammonia is released, the taurine mother liquor can be hydrolyzed into a hydroxyethyl sulfonate solution again or more times under the same conditions; or the mother liquor after concentrating and crystallizing to extract hydroxyethyl sulfonate is hydrolyzed again to be further converted to the hydroxyethyl sulfonate solution. Thus, in the above embodiment, the step (1) can be repeatedly performed for multiple times to form the hydroxyethyl sulfonate solution. The step (1) can also be combined with the step (2) and the step (3) to produce the alkali metal hydroxyethyl sulfonate, and the taurine mother liquor obtained in the step (3) can be recycled for multiple times.

After extensive experiments by the inventors, it was found that a mixture of sodium hydroxyethyl sulfonate and ammonia obtained by the hydrolysis reaction of taurine with sodium hydroxide at 260° C. for 2 hours is a superior choice. Taurine can be subjected to a reverse reaction under a certain condition to produce sodium hydroxyethyl sulfonate and ammonia by hydrolysis. The mother liquor after extraction of taurine contains a certain amount of taurine, sodium hydroxyethyl sulfonate, hydroxyethyl sulfonic acid derivatives, taurine derivatives and so on. Subjecting the mother liquor to a reaction at 260° C. for 2 hours in the present of sodium hydroxide can also obtain sodium hydroxyethyl sulfonate and ammonia. The hydroxyethyl sulfonic acid derivatives and taurine derivatives are hydrolyzed to different degrees to hydroxyethyl sulfonate.

Based on the above, this embodiment describes an example of a method for producing alkali metal hydroxyethyl sulfonate by using taurine mother liquor, in which sodium hydroxide is added in the hydrolysis step, as shown in FIGS. 1 to 3, including:

step (1): a hydrolysis step, including: an appropriate sodium hydroxide is added to the taurine mother liquor, and the obtained mixture is heated to a certain temperature, and subjected to a reaction for a period of time, and the resulting ammonia is continuously discharged and absorbed. Then the solution is appropriately evaporated and concentrated to obtain a sodium hydroxyethyl sulfonate solution having a content of greater than 20%.

Wherein, the hydrolysis is performed at a temperature of 30-350° C. for 0.5 h-50 h, and the amount of sodium hydroxide is at least 0.2 times the equivalent amount of taurine, wherein preferably a molar ratio of taurine in the taurine mother liquor to sodium hydroxide is 1:0.5-1.5.

Step (2): a step of decolorization and removing impurities, including: activated carbon is added into the sodium hydroxyethyl sulfonate solution having the content of greater than 20% for decolorization, with continuous stirring during decolorization, and filtering is carried out when the decolorization is completed.

Further, the step of decolorization and removing impurities is performed at a temperature of 0-100° C. and the stirring is carried out for 0.5-5 h.

Wherein, the step of decolorization and removing impurities is preferably performed at a temperature of 35° C.-65° C.

Step (3): a concentration and crystallization step, including: the decolorized sodium hydroxyethyl sulfonate solution is concentrated and crystallized to obtain a solid sodium hydroxyethyl sulfonate, and a mother liquor. The mother liquor after concentration and crystallization can be purified by crystallization after impurity removal to achieve recycling, or can be returned to the step (1) to be hydrolyzed again.

Wherein, the concentration and crystallization is carried out at 50° C.-80° C.

Further, for other embodiments, the alkali metal hydroxyethyl sulfonate obtained after the hydrolysis of the mother liquor can be used to produce other products such as sodium cocoyl hydroxyethyl sulfonate, sodium lauroyl hydroxyethyl sulfonate, sodium cocoyl methyl taurate, sodium lauroyl methyl taurate, 2-(N-morpholino)ethanesulfonic acid, sodium 2-(N-morpholino)ethanesulfonate, 2-(N-morpholino)ethanesulfonic acid monohydrate, 4-hydroxyethyl piperazinyl ethanesulfonic acid, sodium 4-hydroxyethyl piperazinyl ethanesulfonate, piperazine-N,N'-bis(2-ethanesulfonic acid), dis odium piperazine-N,N'-bis(3-ethanesulfonate), hydroxyethyl sulfonic acid, sodium methyl taurate, methyl taurine, etc., thereby achieving the purpose of the recycling of the taurine mother liquor.

Figure 4:
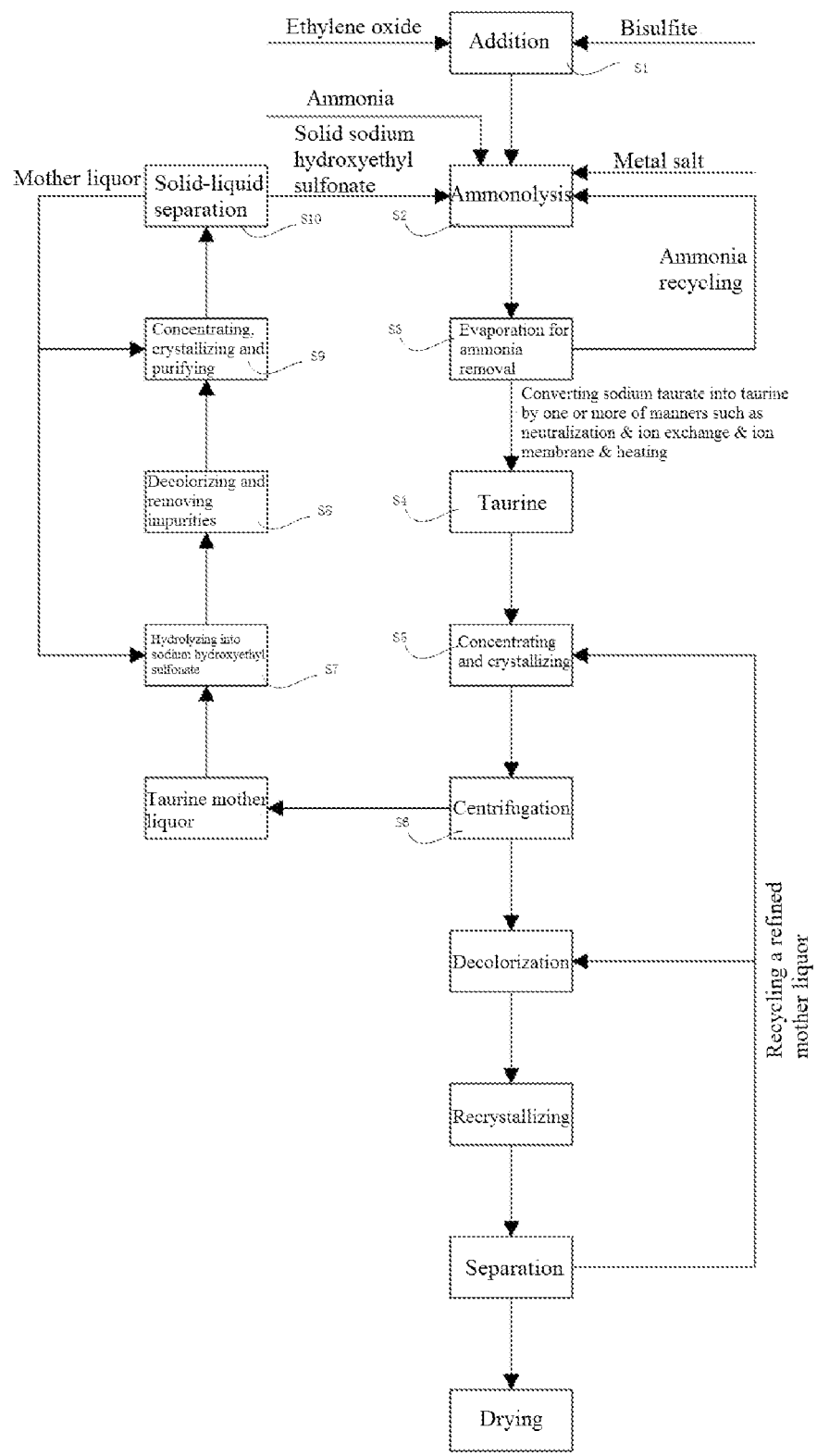
FIG. 4 shows a flow diagram of recycling taurine in a production process of taurine.

As shown in FIG. 4, this embodiment introduces the recycling of the taurine mother liquor by the method for producing the alkali metal hydroxyethyl sulfonate by using the taurine mother liquor in a process for production of taurine by an ethylene oxide method, specifically including:

S1. reacting ethylene oxide with a bisulfite solution to obtain hydroxyethyl sulfonate;

S2. mixing the hydroxyethyl sulfonate obtained in S1 with ammonia in the presence of alkali metal for an ammonolysis reaction;

S3. evaporating to remove excess ammonia after the ammonolysis reaction;

S4. converting the resulting taurate to taurine;

S5. concentrating and crystallizing the obtained taurine solution, and separating crude taurine and a taurine mother liquor; S6. decolorizing, recrystallizing, and separating the crude taurine to obtain a refined taurine product, and drying to obtain a finished taurine product, and returning the refined taurine mother liquor after separating to decolorization or concentrating and crystallizing in S5 for recycling;

S7. adding an appropriate base into the mother liquor after extraction of the crude taurine in S5, then heating and hydrolyzing, evaporating to remove ammonia to obtain a hydroxyethyl sulfonate solution;

S8. decolorizing and removing impurities from the solution obtained in the step S7;

S9. concentrating and crystallizing the solution obtained in the step S8; and

S10. carrying out solid-liquid separation on the crystallization solution obtained in S9 to obtain solid hydroxyethyl sulfonate, wherein the solid hydroxyethyl sulfonate can be returned to the step S2 for recycling, and the mother liquor after solid-liquid separation can be returned to the step S7 or S9 for recycling.

It can be seen that the method for producing the alkali metal hydroxyethyl sulfonate by using the taurine mother liquor of the present disclosure can be used mainly for the recycling of the taurine mother liquor again after concentrating and crystallizing the taurine solution and separating to obtain the crude taurine and the taurine mother liquor in the process of taurine production, which is completed by the above steps S7 to S10.

Of course, actual mother liquor obtaining is not limited to this, but can also be extended to other taurine production processes, as long as there is a production process in which a taurine mother liquor is produced.

The technical effects of the present disclosure are demonstrated below by several different sets of experiments.

1. This embodiment shows an experiment of hydrolysis of taurine in the presence of sodium hydroxide at different temperatures:

62.5 g (0.50 mol) of taurine was added to a 3 L reaction kettle, and dissolved with 1000 ml of purified water, and then 24 g of sodium hydroxide was added. The resulting solution was heated to different temperatures in Table 1, and was subjected to heat preservation while stirring for 2 h. The ammonia gas released during the reaction was absorbed.

TABLE 1

Molar amount of sodium hydroxyethyl sulfonate after reaction at different temperatures

| Temperature (° C.) | Sodium hydroxyethyl sulfonate (mol) |
|---|---|
| 130 | 0.30 |
| 180 | 0.35 |
| 200 | 0.40 |
| 240 | 0.46 |
| 260 | 0.47 |
| 280 | 0.46 |

2. This embodiment shows an experiment of hydrolysis of a taurine mother liquor at different temperatures in the presence of sodium hydroxide:

625 ml of taurine mother liquor which contained 10% of taurine and 15% of sodium hydroxyethyl sulfonate was added to a 3 L reaction kettle, and then dissolved with 1000 ml of purified water, and then 24 g of sodium hydroxide was added. The resulting solution was heated to different temperatures as shown in Table 2, and was subjected to heat preservation while stirring for 2 hours. The ammonia gas released during the reaction was absorbed.

TABLE 2

Molar amount of sodium hydroxyethyl sulfonate
after reaction at different temperatures

| Temperature (° C.) | Sodium hydroxyethyl sulfonate (mol) |
| --- | --- |
| 130 | 1 |
| 180 | 1.05 |
| 200 | 1.15 |
| 240 | 1.2 |
| 260 | 1.25 |
| 280 | 1.3 |

3. This embodiment shows an experiment of hydrolysis of a taurine mother liquor in different alkali metals:

625 ml of taurine mother liquor which contained 10% of taurine and 15% of sodium hydroxyethyl sulfonate was added to a 3 L reaction kettle, and then dissolved with 1000 ml of purified water, and then different alkali metals as shown in Table 3 were added. The resulting solutions were heated to 260° C., and were subjected to heat preservation while stirring for 2 hours. The ammonia gas released during the reaction was absorbed.

TABLE 3

Molar amount of sodium hydroxyethyl sulfonate
after reaction with different alkali metals

| Alkali metal | Added amounts of alkali metal (mol) | Sodium hydroxyethyl sulfonate (mol) |
| --- | --- | --- |
| None | 0 | 0.91 |
| Sodium hydroxide | 0.1 | 1.11 |
| Sodium hydroxide | 0.25 | 1.2 |
| Sodium hydroxide | 0.5 | 1.3 |
| Sodium hydroxide | 0.6 | 1.4 |
| Sodium hydroxide | 0.75 | 1.4 |
| Sodium carbonate | 0.5 | 1.21 |
| Sodium sulfite | 0.5 | 1.19 |
| Potassium hydroxide | 0.5 | 1.22 |
| Potassium carbonate | 0.5 | 1.23 |
| Potassium sulfite | 0.5 | 1.2 |
| Lithium hydroxide | 0.5 | 1.23 |
| Lithium carbonate | 0.5 | 1.2 |

4. This embodiment shows an experiment of the purification and subsequent utilization of sodium hydroxyethyl sulfonate after hydrolysis of a taurine mother liquor:

1250 ml of taurine mother liquor which contained 10% of taurine and 15% of sodium hydroxyethyl sulfonate was added to a 3 L reaction kettle, and then dissolved with 1000 ml of purified water, and then 48 g of sodium hydroxide was added. The resulting solution was subjected to heat preservation while stirring at 260° C. for 2 hours, and the ammonia gas released during the reaction was absorbed. The solution after the reaction was decolorized for impurity removal and then concentrated and crystallized, and extracted once to obtain 235 g of sodium hydroxyethyl sulfonate solid which contains 4.5% of water, 95% of sodium ethyl sulfonate, less than 0.01% of ethylene glycol and less than 0.01% of sulfate ion. Then, the obtained solid was subsequently used to prepare sodium cocoyl hydroxyethyl sulfonate, sodium lauroyl hydroxyethyl sulfonate, sodium cocoyl methyl taurate, sodium lauroyl methyl taurate, 2-(N-morpholino)ethanesulfonic acid, sodium 2-(N-morpholino)ethanesulfonate, 2-(N-morpholine)ethanesulfonic acid monohydrate, 4-hydroxyethyl piperazinyl ethanesulfonic acid, sodium 4-hydroxyethyl piperazinyl ethanesulfonate, piperazine-N,N'-bis (2-ethanesulfonic acid), disodium piperazine-N,N'-bis(3-ethanesulfonate), hydroxyethyl sulfonic acid, sodium methyl taurate, methyl taurine and other products, and the corresponding qualified products can be obtained.

Based on the long-term experimental summary of the inventors, the present disclosure provides the method for producing the alkali metal hydroxyethyl sulfonate solution by using the taurine mother liquor, which is capable of converting the taurine mother liquor into the alkali metal hydroxyethyl sulfonate by hydrolysis, thereby performing various flexible applications of the alkali metal hydroxyethyl sulfonate by a person skilled in the art, and realizing the recycling of the taurine mother liquor.

In addition, the present disclosure further provides a method to realize the recycling of taurine production, in which the taurine mother liquor is converted into the alkali metal hydroxyethyl sulfonate, thereby increasing the content of the alkali metal hydroxyethyl sulfonate, while since the solubility of the alkali metal hydroxyethyl sulfonate is very large, the separation of impurities can be realized by adsorptive decolorization at a reduced temperature, and then the alkali metal hydroxyethyl sulfonate is separated by concentration and crystallization, which further realizes the separation of impurities, thereby obtaining a high content of alkali metal hydroxyethyl sulfonate. The separated alkali metal hydroxyethyl sulfonate can be used as a raw material of taurine. The recycling process for producing the alkali metal hydroxyethyl sulfonate provided by the present disclosure can be discontinuous, semi-continuous or continuous.

In summary, the general method of recycling the taurine mother liquor provided by the present disclosure is an efficient and simple method of separating impurities, very easy to implement industrially, and can effectively recycle the taurine mother liquor.

The above are only preferred embodiments of the present disclosure, and it should be noted that for a person of ordinary skill in the art, a number of improvements and variations can be made without departing from the technical principles of the present disclosure, and these improvements and variations should also be regarded as falling into the protection scope of the present disclosure.

What is claimed is:

1. A method for producing an alkali metal hydroxyethyl sulfonate by using a taurine mother liquor, comprising:
   adding a base to the taurine mother liquor, heating to a first temperature, carrying out a hydrolysis reaction at the first temperature, removing ammonia produced, and evaporating and concentrating the ammonia-removed solution to obtain an alkali metal hydroxyethyl sulfonate solution, wherein the base added is an alkali metal hydroxide, an alkali metal carbonate compound or an alkali metal sulfite compound.

2. The method for producing the alkali metal hydroxyethyl sulfonate by using the taurine mother liquor according to claim 1, comprising:
   removing impurities from the resulting alkali metal hydroxyethyl sulfonate solution, concentrating and crystallizing the impurity-removed alkali metal hydroxyethyl sulfonate solution, and separating the alkali metal hydroxyethyl sulfonate.

3. The method for producing the alkali metal hydroxyethyl sulfonate by using the taurine mother liquor according to claim 1, wherein the first temperature is 20-350° C. and the hydrolysis reaction is carried out for a period of greater than 1 min.

4. The method for producing the alkali metal hydroxyethyl sulfonate by using the taurine mother liquor according to claim 1, wherein the first temperature is 140-280° C. and the hydrolysis reaction is carried out for 0.5-5 hours.

5. The method for producing the alkali metal hydroxyethyl sulfonate by using the taurine mother liquor according to claim 1, wherein the amount of the base is at least 20% of a molar amount of taurine in the mother liquor.

6. The method for producing the alkali metal hydroxyethyl sulfonate by using the taurine mother liquor according to claim 1, wherein a molar ratio of the taurine in the mother liquor to the base is 1:0.5 to 1.5.

7. The method for producing the alkali metal hydroxyethyl sulfonate by using the taurine mother liquor according to claim 2, wherein the method for removing the impurities is performed as follows: adding a decolorizing agent into the resulting alkali metal hydroxyethyl sulfonate solution for decolorization.

8. The method for producing the alkali metal hydroxyethyl sulfonate by using the taurine mother liquor according to claim 7, wherein the decolorizing agent is stirred for 0.5 to 5 h during the process of adding the decolorizing agent for the decolorization.

9. The method for producing the alkali metal hydroxyethyl sulfonate by using the taurine mother liquor according to claim 7, wherein the decolorizing agent is activated carbon or ion exchange resin, and activated carbon decolorization is carried out at 15-95° C.

10. The method for producing the alkali metal hydroxyethyl sulfonate by using the taurine mother liquor according to claim 7, wherein the decolorizing agent is activated carbon or ion exchange resin, and activated carbon decolorization is carried out at 35° C.-65° C.

11. The method for producing the alkali metal hydroxyethyl sulfonate by using the taurine mother liquor according to claim 2, wherein the concentrating and crystallizing is carried out at 20° C.-80° C.

12. The method for producing the alkali metal hydroxyethyl sulfonate by using the taurine mother liquor according to claim 1, wherein the base added is an alkali metal hydroxide.

13. The method for producing the alkali metal hydroxyethyl sulfonate by using the taurine mother liquor according to claim 1, wherein the base added is a sodium hydroxide.

14. The method for producing the alkali metal hydroxyethyl sulfonate by using the taurine mother liquor according to claim 1, wherein ammonia is continuously removed during the conversion of the taurine mother liquor into the alkali metal hydroxyethyl sulfonate solution.

15. The method for producing the alkali metal hydroxyethyl sulfonate by using the taurine mother liquor according to claim 2, further comprising using the separated alkali metal hydroxyethyl sulfonate to prepare sodium cocoyl hydroxyethyl sulfonate, sodium lauroyl hydroxyethyl sulfonate, sodium cocoyl methyl taurate, sodium lauroyl methyl taurate, 2-(N-morpholino)ethanesulfonic acid, sodium 2-(N-morpholino)ethanesulfonate, 2-(N-morpholino)ethanesulfonic acid monohydrate, 4-hydroxyethyl piperazinyl ethanesulfonic acid, sodium 4-hydroxyethyl piperazinyl ethanesulfonate, piperazine-N,N'-bis(2-ethanesulfonic acid), disodium piperazine-N,N'-bis(3-ethanesulfonate), hydroxyethyl sulfonic acid, sodium methyl taurate, methyl taurine and/or taurine.

16. The method for producing the alkali metal hydroxyethyl sulfonate by using the taurine mother liquor according to claim 2, further comprising: obtaining the taurine mother liquor by removing the separated alkali metal hydroxyethyl sulfonate.

17. The method for producing the alkali metal hydroxyethyl sulfonate by using the taurine mother liquor according to claim 2, further comprising:
    subjecting the separated alkali metal hydroxyethyl sulfonate to ammonolysis in an ethylene oxide method to produce taurine.

18. The method for producing the alkali metal hydroxyethyl sulfonate by using the taurine mother liquor according to claim 1, wherein the mass-volume percentage content of the alkali metal hydroxyethyl sulfonate in the alkali metal hydroxyethyl sulfonate solution is greater than 20%.

19. The method for producing the alkali metal hydroxyethyl sulfonate by using the taurine mother liquor according to claim 7, wherein the decolorizing agent is activated carbon or ion exchange resin, and activated carbon decolorization is carried out at 35° C.-65° C.

\* \* \* \* \*